United States Patent [19]

Sasaki et al.

[11] Patent Number: 5,211,738
[45] Date of Patent: May 18, 1993

[54] ADENINE DERIVATIVES AND THEIR USE AS A PLANT GROWTH REGULATOR

[75] Inventors: Yoshinori Sasaki, Ooita; Takashi Oritani, Toyama; Akinori Tanaka, Niigata; Taketo Maruyama, Niigata; Mitsunori Oda, Niigata; Takashi Suzuki, Niigata; Yoshiaki Suzuki, Niigata; Masakazu Furushima, Tokyo, all of Japan

[73] Assignee: Mitsubishi Gas Chemical Co., Inc., Tokyo, Japan

[21] Appl. No.: 861,771

[22] Filed: Apr. 2, 1992

[30] Foreign Application Priority Data

Apr. 12, 1991 [JP] Japan .................................. 3-108844
Oct. 31, 1991 [JP] Japan .................................. 3-314072

[51] Int. Cl.$^5$ .................... C07D 473/34; A01M 43/54
[52] U.S. Cl. .................................... 504/241; 544/277; 504/185
[58] Field of Search ...................... 544/277, 276; 71/92

[56] References Cited

U.S. PATENT DOCUMENTS 4,718,936  1/1988  Bliesener et al. .................... 71/92

FOREIGN PATENT DOCUMENTS 0390515  10/1990  European Pat. Off. .
2-255682   3/1989  Japan .
2-255683   3/1989  Japan .
  45290    4/1990  Japan .

OTHER PUBLICATIONS

"Phytochemistry" 16, 1865–1869, 1977, J. Roussaux, et al.
"Phytochemistry" 10, 305–314, 1971, J. Roussaux, et al., Activite Cytokinine' De OuelOues Derives Analogues: Isosteres Azotes Et Isomeres De La Triacanthine.
"Phytochemistry" 19, 2239–2253, 1980, Satoshi Matsubara, Structure–Activity Relationships of Cytokinins.
"J. Plant Physiol." 123, 55–67, 1986, J. Roussaux, et al. Inhibition of Mitochondrial Oxidations by Adenine–derivatives and Auxin Related Compounds.
"Physiol. Plant". 49, 304–314, 1980, Frank Wightman, et al. Hormonal factors controlling the initiation and development of lateral roots.
"Physiol. Plant". 80, 534–540, 1990, Marie Bollmark, et al., Ethylene accelerates the breakdown of cytokinins and thereby stimulates rooting in Norway spruce hypocotyl cuttings.
"J. Plant Physiol". 132, 262–265, 1988, Marie Bollmark, et al. Variation in Endogenous Cytokinin Content during Adventitious Root Formation in Pea Cuttings.

Primary Examiner—Nicholas S. Rizzo
Attorney, Agent, or Firm—Wyatt, Gerber, Burke and Badie

[57] ABSTRACT

A denine derivatives represented by the following formula:

$$\text{HN}-(\text{CH}_2)_n-\underset{\underset{R}{|}}{C}=N-OR'$$

(with adenine ring system)

(wherein n is 1 or 2 and R and R' represent hydrogen or a methyl, ethyl, allyl, or propargyl group) and agriculturally acceptable acid addition salts thereof, which have cytokinin activity and besides, excellent rooting action, is applied to as plant growth regulators.

7 Claims, No Drawings

ADENINE DERIVATIVES AND THEIR USE AS A PLANT GROWTH REGULATOR

The present invention relates to adenine derivatives represented by the following formula (1):

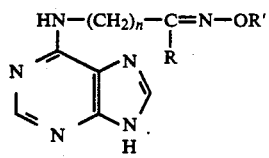

(wherein n represents 1 or 2 and R and R' each represents a hydrogen atom or a methyl, ethyl, allyl or propargyl group).

The adenine derivatives of the present invention show cytokinin activity and are useful for acceleration of plant physiological actions such as acceleration of plant cell division, promotion of growth of lateral buds and fruits, stimulation of seed germination and bud formation, acceleration of blooming and fruit bearing, senescence retardation and promotion of substance accumulation in storage organs. Moreover, the adenine derivatives of the present invention have a stimulating activity of root formation in addition to cytokinin activity.

Hitherto, many compounds have been proposed for regulation of vegetation of plants, especially cereals, fruits and vegetables. Among them, compounds generically called cytokinins are known to have many physiological activities and typical examples thereof are zeatin, kinetin and benzyladenine(6-benzylaminopurin). These cytokinins are known to have plant physiological activities such acceleration of plant cell division, promotion of growth of lateral buds and fruits, stimulation of seed germination and bud formation and acceleration of blooming and fruit bearing, senescence retardation and promotion of substance accumulation in storage organs. It is also known that rooting can be further stimulated by using auxins, but it is well known that there are many plants which cannot be or are hardly stimulated by such method. Furthermore, compounds having cytokinin activity which have hitherto been found have substantially no action of stimulating root formation.

Benzyladenines represented by the following formula (2) have been known as cytokinin compounds utilized in the field of agriculture, but are not wide in their applicability in practical use and more effective compounds have been demanded. Besides, more effective rooting stimulators have also been desired.

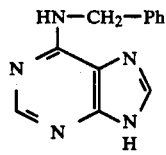

(wherein Ph represents a phenyl group).

An object of the present invention is to provide novel substances which have cytokinin activity and rooting action superior to those of known adenine derivatives and can be utilized in a wide variety of uses, namely, to provide excellent plant growth regulators.

The inventors have conducted intensive research on synthesis of compounds having various substituents on $N^6$ nitrogen atom of adenines and screening of biological activity thereof and as a result they have found that the novel adenine derivatives represented by the following formula (1) have both the excellent cytokinin activity and the action of stimulating root formation. Thus, the present invention has been accomplished.

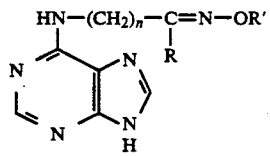

(wherein n represents 1 or 2 and R and R' each represents hydrogen or a methyl, ethyl, allyl or propargyl group.).

That is, the present invention relates to adenine derivatives represented by the above formula (1).

The adenine derivatives represented by the above formula can be obtained, for example, by the following process.

6-Chloropurine and an amine compound having the structure represented by the following formula (3) are heated in organic solvents such as alcohols in the presence of trialkylamines such as ethyldiisopropylamine to allow 6-chloropurine and the amine compound to react with each other.

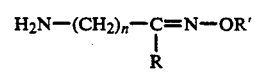

(wherein n represents 1 or 2 and R and R' each represents hydrogen or a methyl, ethyl, allyl or propargyl group).

The amine compounds represented by the formula (3) can be obtained, for example, by deprotecting phthalimides represented by the formula (5) which are obtained by allowing N-(oxoalkyl)phthalimides represented by the formula (4) to react with hydroxylamine or O-substituted hydroxylamines. The deprotection can be carried out by reaction with acids such as hydrochloric acid and hydrobromic acid or hydrazine.

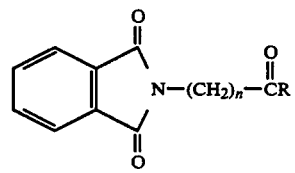

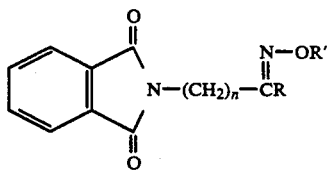

(wherein n represents 1 or 2 and R and R' each represents hydrogen or a methyl, ethyl, allyl or propargyl group).

Typical examples of the adenine derivatives represented by the formula (1) are as follows.

$N^6$-[2-(N-methoxyimino)ethyl]adenine represented by the following formula (6):

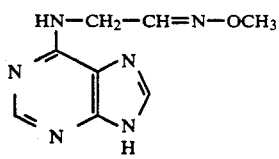
(6)

$N^6$-[2-(N-methoxyimino)propyl]adenine represented by the following formula (7):

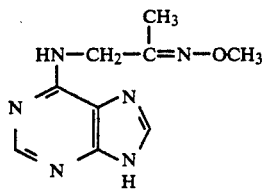
(7)

$N^6$-[3-(N-hydroxyimino)butyl]adenine represented by the following formula (8):

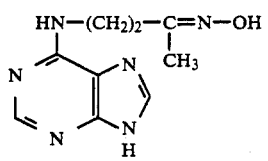
(8)

$N^6$-[3-(N-methoxyimino)butyl]adenine represented by the following formula (9):

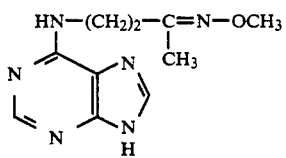
(9)

$N^6$-[2-(N-ethoxyimino)propyl]adenine represented by the following formula (10):

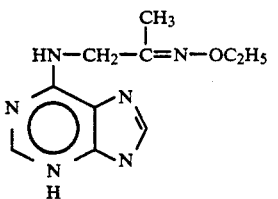
(10)

$N^6$-[2-(N-allyloxyimino)propyl]adenine represented by the following formula (11):

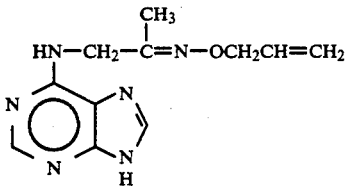
(11)

$N^6$-[2-(N-propaglyoxyimino)propyl]adenine represented by the following formula (12):

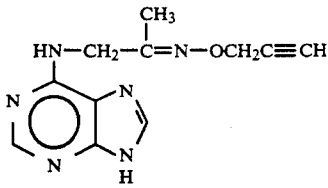
(12)

The adenine derivatives of the present invention can be easily converted to salts of mineral acids such as hydrochloric acid, hydrobromic acid, sulfuric acid, nitric acid and phosphoric acid or salts of organic acids such as formic acid and acetic acid which are represented by the following formula (13) by conventional process

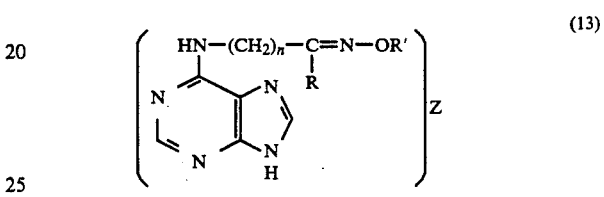
(13)

(wherein n represents 1 or 2, R and R' each represents hydrogen or a methyl, ethyl, allyl or propargyl group and Z represents an equivalent amount of an acid such as hydrochloric acid, hydrobromic acid, sulfuric acid, nitric acid, phosphoric acid, formic acid or acetic acid).

Physical properties of the adenine derivatives represented by the formula (1) are shown in Table 1.

TABLE 1

| Compound No. | Formula | n | R | R' | mp(°C.) |
|---|---|---|---|---|---|
| A | (6) | 1 | H | $CH_3$ | 239–246 decomposition |
| B | (7) | 1 | $CH_3$ | $CH_3$ | 220–227 decomposition |
| C | (8) | 2 | $CH_3$ | H | 216–238 |
| D | (9) | 2 | $CH_3$ | $CH_3$ | 189–201 |
| E | (10) | 1 | $CH_3$ | $C_2H_5$ | 226–228 |
| F | (11) | 1 | $CH_3$ | $CH_2CH=CH_2$ | 206–208 |
| G | (12) | 1 | $CH_3$ | $CH_2C\equiv CH$ | 194–196 |

The adenine derivatives represented by the formula (1) and salts thereof represented by the formula (13) have plant hormone activity and cytokinin activity, and stimulate root formation, and therefore are expected to be able to be used as plant growth regulators in the fields or as medium components for culturing of plant tissue.

These compounds per se can be used alone or as the active ingredient in a composition for plant growth regulator. Typically, they are used in combination with agriculturally acceptable liquid or solid carriers and, optionally, with surface active agents as emulsifiers, dispersants, spreaders, and stickers such as those which are generally used in the field of formulation of agrochemicals.

Examples of formulations within the scope of the invention are emulsifiable concentrates, wettable powders, dusts and liquids.

As diluents for preparation of a liquid formulation, mention may be made of polar solvents such as alcohols, e.g., methanol and ethanol, water, dimethylformadmide and dimethylsulfoxide.

As carriers for preparation of a wettable powder, granule or dust, there may be used talc, clay, bentonite, kaolin, montmorilonite, diatomaceous earth, phenol resin and white carbon.

Typical examples of surface-active agents which may be usefully employed in the practice of the invention are anionic surface-active agents such as sodium alkylbenzene-sulfonates and sodium laurylsulfate, cationic surface-active agents such as stearyltrimethylammonium chloride and nonionic surface-active agents such as polyoxyethylenealkylphenyl ether.

As dispersants, there may be used, in addition to the above surface-active agents, for example, sodium ligninsulfonate, methyl cellulose, and sulfite waste liquor.

As stickers i.e. materials to adhere the active agents to the plants, there may be used, for example, casein lime, glue, carboxymethyl cellulose, sodium alginate and polyvinyl alcohol.

When the composition of the present invention is used as rooting stimulators, there may be employed the method of immersing a cutting of plant in an aqueous solution of the compound and then planting the cutting in nursery or the method of coating or covering a cut section of a cutting with the composition. Furthermore, other rooting stimulators such as indoleacetic acid, indolebutyric acid, naphthylacetic acid and 2,4-dichlorophenoxyacetic acid which are plant hormones, and fungicides and fertilizers may be used in combination with the composition of the present invention and further enhancement of the effects and labor-saving can be attained thereby.

The composition of the present invention can be applied, as plant growth regulators, to fruit trees such as grapevine, mandarin, pear tree, and peach tree, woods such as oak, pine, and Japanese cypress, and flowering plants such as camellia, rhododendron, azalea, chrysanthemum, carnation, rose and poinsettia.

Synthesis of the adenine derivatives of the present invention and physiological activities thereof will be illustrated by the following examples and test examples.

EXAMPLE 1

Synthesis of $N^6$-[2-(N-methoxyimino)ethyl]adenine (compound A)

A branched chain amine compound was first synthesized and then, this was allowed to react with 6-chloropurine in the following manner.

(1) Synthesis of N-[2-(N-methoxyimino)ethyl]phthalimide 0.560 g (2.96 mmol) of N-(2-oxoethyl)phthalimide was dissolved in 20 ml of ethanol and to the solution was added 0.330 g (3.95 mmol) of O-methylhydroxylamine hydrochloride. To this suspension was added 10 ml of 0.35M aqueous sodium carbonate solution, followed by being stirred at room temperature for 3 days. The reaction mixture was poured into 100 ml of water and extracted with chloroform (20 ml×3), and the combined organic layer was dried over magnesium sulfate. Chloroform was distilled off and the residual solids were washed with petroleum ether to give 0.291 g (yield 45%) of the titled compound as colorless crystals.

(2) Synthesis of $N^6$-[2-(N-methoxyimino)ethyl]adenine (compound A)

0.290 g (1.33 mmol) of N-[(2-(N-methoxyimino)ethyl]phthalimide was dissolved in 8 ml of ethanol and to the solution was added 77.7 μl (1.60 mmol) of hydrazine hydrate, followed by being refluxed for 5 hours. The reaction mixture was cooled to room temperature and then, 15 ml of ether was added thereto and the mixture was left to stand at 0° C. for 1 hour to sufficiently precipitate solids. The solids were removed by suction filtration and the filtrate was dried over sodium sulfate and concentrated to 1 ml by an avaporator. This concentrated filtrate was dissolved in 5 ml of isopropanol and to the solution were added 77.7 mg (0.503 mmol) of 6-chloropurine and 88 μl of ethyldiisopropylamine, followed by being refluxed with heating on an oil bath for 5 hours. The precipitated crystals were collected by filtration and thereafter, were purified by a thin layer chromatography (silica gel, developing agent: 10% ethanolchloroform) to give 5.2 mg (yield 2%) of the titled compound as a white powder.

$^1$H-NMR spectrum (DMSO-d$_6$, TMS as internal standard); δ=3.77(s, 3H×0.5), 3.88(s, 3H×0.5), 4.37(m, 2H), 6.86(t, J=3.7 Hz, 1H×0.5), 7.53(t, J=5.4 Hz, 1H×0.5), 8.17(s, 1H), 8.23(s, 1H), 12.90(br, 1H)ppm, IR spectrum (KBr); νmax=2900$^s$, 2700$^{vs}$, 2660$^s$, 1570$^s$, 1435$^m$, 1390$^m$, 1295$^m$, 1240$^m$, 1045$^w$, 1010$^w$, 885$^m$, 855$^m$, 825$^m$, 725$^w$, 630$^w$cm$^{-1}$, UV spectrum: λmax(H$_2$O)=208(24,600), 266(20,800)nm; λmax(0.1 NHCl)=207(20,600)nm; λmax(0.1 NNaOH)=272(18,400), 280$^{sh}$(13,800)nm, Elemental analysis; C$_8$H$_{10}$N$_6$O; Calcd. C:46.60% H:4.89% N:10.76%, Found C:46.95% H:5.08% N:40.33%.

EXAMPLE 2

Synthesis of $N^6$-[2-(N-methoxyimino)propyl]adenine (compound B)

A branched chain amine compound was first synthesized and then, this was allowed to react with 6-chloropurine in the following manner.

(1) Synthesis of N-[2-(N-methoxyimino)propyl]-phthalimide 1.33 g (6.55 mmol) of N-(2-oxopropyl)phthalimide was dissolved in 30 ml of ethanol and to the solution was added 1.64 g (19.7 mmol) of O-methylhydroxylamine hydrochloride. To this suspension was added 20 ml of 2N aqueous sodium hydroxide solution, followed by being stirred at room temperature for 12 hours. The reaction mixture was poured into 100 ml of water and extracted with chloroform (30 ml×3), and the combined organic layer was dried over magnesium sulfate. Chloroform was distilled off and the residual solids were washed with hexane to give 1.03 g (yield 68%) of the titled compound as colorless crystals.

Melting point 114°-131° C., $^1$H-NMR spectrum (DMSO-d$_6$, TMS as internal standard); δ=1.83(s, 3H), 3.73(s, 3H), 4.35(m, 2H), 7.82(s, 4H)ppm, IR spectrum (KBr); νmax=2870$^w$, 1680$^s$, 1360$^s$, 1315$^s$, 1035$^s$, 900$^w$, 825$^m$, 695$^m$cm$^{-1}$, (2) Synthesis of N6-[2-(N-methoxyimino)propyl]adenine (compound B)

0.232 g (1.00 mmol) of N-[2-(N-methoxyimino)propyl]phthalimide was dissolved in 6 ml of methanol and to the solution was added 60 μl (1.2 mmol) of hydrazine hydrate, followed by being refluxed for 5 hours. The reaction mixture was cooled to room temperature and then, 20 ml of ether was added thereto and the mixture was left to stand at 0° C. for 1 hour to sufficiently precipitate solids. The solids were removed by suction filtration and the filtrate was dried over sodium sulfate and concentrated to 1 ml by an evaporator. This concentrated filtrate was dissolved in 5 ml of isopropanol and to the solution were added 105 mg (0.680 mmol) of 6-chloropurine and 101 μl of ethyldiisopropylamine, followed by being refluxed with heating on an oil bath for 5 hours. The reaction mixture was poured into 20 ml of water and extracted with chloroform (15 ml×5). The extract was dried over magnesium sulfate and the solvent was distilled off. The residue was purified by a thin layer chromatography (silica gel, developing agent: 15% ethanol-chloroform) to give 32.0 mg (yield 15%) of the titled compound as white solids.

$^1$H-NMR spectrum (DMSO-$d_6$, TMS as internal standard); δ=1.72(s, 3H×0.14), 1.79(s, 3H×0.86), 3.74(s, 3H), 4.28(d, J=6 Hz, 2H), 7.63(t-like, J=6 Hz, 1H), 8.07(s, 1H), 8.17(s, 1H), 12.70(br, 1H)ppm, IR spectrum (KBr); νmax=2910$^s$, 2770$^{br}$, 1585$^{vs}$, 1245$^m$, 1130$^w$, 1035$^m$, 880$^m$, 625$^w$cm$^{-1}$.

UV spectrum: λmax(H$_2$O)=208(30,800), 266(24,000)nm; λmax(0.1NHCl)=275(15,700)nm; λmax(0.1NNaOH)=273(15,900), 280$^{sn}$(12,400)nm.

Elemental analysis; C$_9$H$_{12}$N$_6$O; Calcd. C:49.08% H:5.49% N:38.16%, Found C:49.29% H:5.77% N:38.50%.

EXAMPLE 3

Synthesis of N6-[3-(N-hydroxyimino)butyl]adenine (compound C)

A branched chain amine compound was first synthesized and then, this was allowed to react with 6-chloropurine in the following manner.

(1) Synthesis of N-[3-(N-hydroxyimino)butyl]-phthalimide 1.08 g (5.00 mmol) of N-(3-oxobutyl)phthalimide was dissolved in 10 ml of methanol and to the solution was added 0.695 g (10.0 mmol) of hydroxylamine hydrochloride. To this suspension was added 2 ml of 5N aqueous sodium hydroxide solution, followed by being stirred at room temperature for 16 hours. The reaction mixture was poured into 100 ml of saturated aqueous sodium hydrogencarbonate and extracted with chloroform (30 ml×3), and the combined organic layer was dried over magnesium sulfate. Chloroform was distilled off and the residual solids were washed with hexane to give 0.98 g (yield 84%) of the titled compound as colorless crystals.

Melting point 151°-172° C., $^1$H-NMR spectrum (DMSO-$d_6$, TMS as internal standard); δ=1.81(s, 3H×0.75), 1.83(s, 3H×0.25), 2.3-2.6(m, 2H), 3.78(t, J=6 Hz, 2H×0.75), 3.91(t, J=6 Hz, 2H×0.25), 7.85(s, 4H), 10.15(bs, 1H×0.75), 10.34(s, 1H×0.25)ppm, (2) Synthesis of N6-[3-(N-hydroxyimino)butyl]adenine (compound C)

0.232 g (1.00 mmol) of N-[3-(N-hydroxyimino)butyl]phthalimide was dissolved in 6 ml of methanol and to the solution was added 60 μl (1.2 mmol) of hydrazine hydrate, followed by being refluxed for 5 hours. The reaction mixture was cooled to room temperature and then, 20 ml of ether was added thereto and the mixture was left to stand at 0° C. for 1 hour to sufficiently precipitate solids. The solids were removed by suction filtration and the filtrate was dried over sodium sulfate and concentrated to 1 ml by an evaporator. This concentrated filtrate was dissolved in 5 ml of isopropanol and to the solution were added 75 mg (0.50 mmol) of 6-chloropurine and 101 μl of ethyldiisopropylamine, followed by being refluxed on an oil bath for 5 hours. The reaction mixture was poured into 20 ml of water and extracted with chloroform (15 ml×5). The extract was dried over magnesium sulfate and the solvent was distilled off. The residue was purified by a thin layer chromatography (silica gel, developing agent: 15% ethanol-chloroform) to give 45.1 mg (yield 22%) of the titled compound as white solids.

$^1$H-NMR spectrum (DMSO-$d_6$, TMS as internal standard); δ=1.80(s, 3H), 3.30(m, 2H), 3.69(m, 2H), 7.45(m, 1H), 8.08(s, 1H), 8.19(s, 1H), 10.29(br, 1H), 12.70(br, 1H)ppm, IR spectrum (KBr); νmax=2900$^{br,vs}$, 2810$^s$, 1590$^s$, 1405$^m$, 1300$^m$, 1255$^s$, 1160$^m$, 930$^m$ 885$^m$, 635$^m$cm$^{-1}$, UV spectrum: λmax(H$_2$O)=208(26,100), 267(19,100)nm; λmax(0.1NHCl)=269(20,100)nm; λmax(0.1NNaOH)=273(20,900), 282$^{sn}$(15,800)nm, Elemental analysis; C$_9$H$_{12}$N$_6$O; Calcd. C:49.08% H:5.49% N:38.16%, Found C:49.32% H:5.78% N:37.88%,

EXAMPLE 4

Synthesis of N6-[3-(N-methoxyimino)butyl]adenine (compound D)

A branched chain amine compound was first synthesized and then, this was allowed to react with 6-chloropurine in the following manner.

(1) Synthesis of N-[3-(N-methoxyimino)butyl]-phthalimide 1.08 g (5.00 mmol) of N-(3-oxobutyl)phthalimide was dissolved in 10 ml of methanol and to the solution was added 0.835 g (10.0 mmol) of O-methylhydroxylamine hydrochloride. To this suspension was added 2 ml of 5N aqueous sodium hydroxide solution, followed by being stirred at room temperature for 16 hours. The reaction mixture was poured into 100 ml of saturated aqueous sodium hydrogencarbonate solution and extracted with chloroform (30 ml×3), and the combined organic layer was dried over magnesium sulfate. Chloroform was distilled off and the residual solids were washed with hexane to give 1.23 g (yield 100%) of the titled compound as white crystals.

Melting point 55°-64° C., $^1$H-NMR spectrum (DMSO-$d_6$, TMS as internal standard); δ=1.86(s, 3H×0.66), 1.91(s, 3H×0.34), 2.5(t, J=6 Hz, 2H×0.66), 2.66(t, J=6 Hz, 2H×0.34), 3.48(s, 3H×0.34), 3.65(s, 3H×0.66), 3.84(t, J=6 Hz, 2H×0.66), 3.87(t, J=6 Hz, 2H×0.034), 7.85(s, 4H)ppm,

(2) Synthesis of N⁶-[3-(N-methoxyimino)butyl]adenine (compound D)

0.282 g (1.00 mmol) of N-[3-(N-methoxyimino)butyl]phthalimide was dissolved in 6 ml of methanol and to the solution was added 60 μl (1.2 mmol) of hydrazine hydrate, followed by being refluxed for 7 hours. The reaction mixture was cooled to room temperature and then, 20 ml of ether was added thereto and the mixture was left to stand at 0° C. for 1 hour to sufficiently precipitate solids. The solids were removed by suction filtration and the filtrate was dried over sodium sulfate and concentrated to 1 ml by an evaporator. This concentrated filtrate was dissolved in 5 ml of isopropanol and to the solution were added 105 mg (0.680 mmol) of 6-chloropurine and 101 μl of ethyldiisopropylamine, followed by being refluxed on an oil bath for 5 hours. The reaction mixture was poured into 20 ml of water and extracted with chloroform (15 ml×5). The extract was dried over magnesium sulfate and the solvent was distilled off. The residue was purified by a thin layer chromatography (alumina, developing agent: 15% ethanol-chloroform) to give 85 mg (yield 35%) of the titled compound as white solids.

$^1$H-NMR spectrum (DMSO-d$_6$, TMS as internal standard); δ=1.84(s, 3H), 2.47(t, J=6.5 Hz, 2H), 3.55(m, 2H), 3.70(s, 3H×0.7), 3.74(s, 3H×0.3), 7.44(br, 1H), 8.05(s, 1H), 8.17(s, 1H), 12.60(br, 1H)ppm, IR spectrum (KBr); νmax=3160$^{sn,m}$, 3050$^m$, 2900$^s$, 2770$^s$, 1580$^v$, 1280$^m$, 1240$^m$, 1125$^w$, 1020$^m$, 915$^w$, 870$^m$, 780$^w$, 625$^w$cm$^{-1}$, UV spectrum: λmax(H$_2$O)=206(26,200), 268(15,000)nm; λmax(0.1NHCl)=274(14,100)nm; λmax(0.1NNaOH)=274(14,500), 282$^{sn}$(11,300)nm, Elemental analysis; C$_{10}$H$_{14}$N$_6$O: Calcd. C:51.27% H:6.02% N:35.87%, Found C:51.49% H:6.39% N:35.51%,

Test Example 1 Cytokinin activity test based on the chlorophyll retention effect Rice seeds (var.: Nankin No. 11) were sown in the cultivation soil filled in a seed box and raised for about 1 month in a greenhouse (25° C. in the daytime/15° C. in the nighttime).

Leaf sections of 1 cm long were cut off from the central portion of the fourth leaves of seedlings in the sixth leaf stage. A group of five leaf sections cut off from the seedlings were floated on 2 ml of test solution containing a given concentration of the test compound in a glass tubular bottle having an inner diameter of 32 mm. Three bottles each containing five leaf sections and 2 ml of the test solution were used for each concentration tested. These bottles were placed in the dark at 30° C. for 3 days and thereafter, the leaf sections were put in a test tube containing 10 ml of 80% ethanol and this test tube was dipped in a water bath of 80° C. for 20 minutes to extract chlorophyll.

After cooling, 80% ethanol was added to make up 10 ml and absorbance of the solution was measured with a wavelength of 665 nm.

Senescence retardation rate based on the degree of chlorophyll retention effect caused by test compounds was obtained by the following formula.

The results are shown in Table 2.

$$\text{Senescence retardation rate (\%)} = \frac{a - b}{c - b} \times 100$$

a: Absorbance of the treated group after lapse of 3 days.
b: Absorbance of the untreated group after lapse of 3 days.
c: Absorbance of the leaves before treated.

TABLE 2

| | Cytokinin activity test based on chlorophyll retention effect | | |
|---|---|---|---|
| | Senescence retardation rate (%) Concentration (mg/l) | | |
| Compound | 0.1 | 1 | 10 |
| B | 92 | 96 | 98 |
| Benzyladenine | 82 | 95 | 96 |

Test Example 2 Cytokinin activity test based on soybean hypocotyl section growth Soybean seeds (var.: Enrei) were disinfected with antiformin containing 1% effective chlorine for 12 minutes and washed with sterile water six times. 15 ml of 1.6% agar was put in a test tube of 2.5 cm in diameter and a groove was made on the surface by a forceps. Then, one seed disinfected above was placed therein and left to stand in the dark at 30° C. for 5 days in the dark. In a glass tubular bottle of 26 mm in inner diameter was put 10 ml of Miller's culture medium containing a given concentration of the test compound, benzyladenine or trans Zeatine, and 2,4-D. The central portion of the hypocotyl budding out of the seed was cut at a thickness of 1 mm and the four sections as one group were transplanted onto the Miller's culture medium. Three bottles each containing four leaf sections and 10 ml of the Miller's culture medium were used for each concentration tested. They were placed in the dark at 30° C. for 3 weeks and thereafter, fresh weight of the callus was measured.

The results are shown in Tables 3 and 4.

TABLE 3

| | Cytokinin activity test based on acceleration of cell division of soybean callus | | |
|---|---|---|---|
| | Fresh weight of soybean callus (mg/flask) Concentration (mg/l) | | |
| Compound | 0 | 1 | 10 |
| B | — | 874 | 741 |
| Benzyladenine | — | 809 | 636 |
| Untreated | 86 | | |

2,4-D concentration: 2 mg/l

TABLE 4

| | Cytokinin activity test based on acceleration of cell division of soybean callus | | | |
|---|---|---|---|---|
| | Fresh weight of soybean callus (mg/flask) Concentration (μM) | | | |
| Compound | 0 | 0.1 | 1 | 10 |
| B | — | 661 | 986 | 1167 |
| E | — | 585 | 715 | 1062 |
| trans Zeatine | — | 502 | 730 | 1003 |
| Untreated | 132 | | | |

2,4-D concentration: 2 μM

Test Example 3 Tests on absorption and translocation in rice; Chlorophyll retention effects by penetration of compound B and benzyladenine into rice leaves Rice seeds (var.: Nankin No. 11) were sown in cultivation soil in a seed box and raised for about 1 month in a greenhouse (25° C. in the daytime/15° C. in the nighttime).

Leaf sections of 30 mm in length were cut off from the central portion of the fifth leaves of seedlings in seventh leaf stage. The bottom of a petri dish was covered with one circular filter paper, which was wetted with 2.5 ml of distilled water. A slide glass was put on the filter paper and the five leaf sections were arranged on the slide glass with the back of the leaves facing upward. 10 μl of a test solution prepared by dissolving, at a given concentration, the test compound in 0.1% aqueous solution of Tween 20 was put on the central portion of the respective leaf sections. Three dishes each containing five leaf sections were used for each concentration tested. These petri dishes were covered and then left in the dark at 30° C. for 5 days. Length of the green portion which remained due to the chlorophyll-retaining effect of the test solution was measured.

The results are shown in Table 5.

Comparison of the results on the test solutions of the same concentration revealed that compound B gave the larger green portion than benzyladenine. This indicates that compound B is superior in absorbability and translocation.

TABLE 5

| Test on absorbability and translocation in rice | | |
|---|---|---|
| | | Length of green portion (mm) |
| Benzyladenine | 1 (mg/l) | 18.3 |
| | 10 (mg/l) | 18.1 |
| Compound B | 1 (mg/l) | 20.9 |
| | 10 (mg/l) | 24.3 |

Test Example 4

Shoots of Oak subjected to aseptic subcultivation were planted in a WP culture medium (0.3% "gelrite", 1% sucrose) containing a given concentration of N⁶-[2-(N-methoxyimino)propyl]adenine compound B and were cultivated for 8 weeks with 16 hours in the light of 4,000 lux and 8 hours in the dark per one day at 25°±1° C. Benzyladenine having known cytokinin activity and indolebutyric acid known as a rooting stimulator were used for control test. The results are shown in Table 6.

TABLE 6

| Rooting stimulator effect of N⁶-{2-(N-methoxyimino)propyl}adenine(compound B)on shoots of oak. | | | | |
|---|---|---|---|---|
| Test compounds | Concentration (mg/l) | Number of planted shoots | Number of rooted shoots | Rooting rate (%) |
| Compound B | 0.02 | 81 | 51 | 63 |
| | 0.05 | 92 | 53 | 58 |
| | 0.1 | 94 | 48 | 51 |
| BA | 0.1 | 88 | 1 | 1 |
| IBA | 0.1 | 75 | 25 | 33 |

BA: Benzyladenine, IBA: Indolebutyric acid
Rooting rate = (Number of rooted shoots/number of planted shoots) × 100

We claim:

1. An adenine derivative represented by the formula:

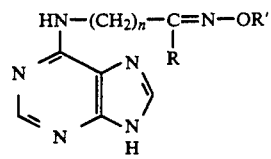

(wherein n represents 1 or 2, and R and R' represent hydrogen or a methyl, ethyl, allyl, or propargyl group) and agriculturally acceptable acid addition salts thereof.

2. An adenine derivative according to claim 1 which is represented by the formula:

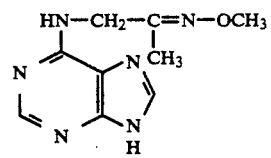

and agriculturally acceptable acid addition salts thereof.

3. A composition comprising an agriculturally acceptable carrier and, as an active ingredient, an effective amount of an adenine derivative represented by the formula:

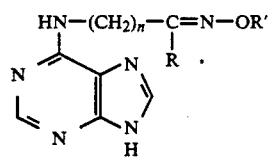

(wherein n represents 1 or 2, and R and R' represent hydrogen or a methyl, ethyl, allyl, or propargyl group) or agriculturally acceptable acid addition salts thereof.

4. A composition according to claim 3 which comprises an agriculturally acceptable carrier and, as an active ingredient, an effective amount of an adenine derivative represented by the formula:

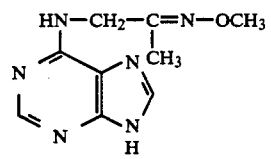

or agriculturally acceptable acid addition salts thereof.

5. A method of using an adenine derivative represented by the formula:

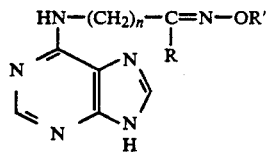

(wherein n represents 1 or 2, and R and R' represent hydrogen or a methyl, ethyl, allyl, or propargyl group) or agriculturally acceptable acid addition salts thereof as a plant growth regulator.

6. A method according to claim 5 which uses an adenine derivative represented by the formula:

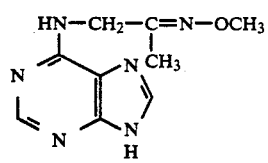
or agriculturally acceptable acid addition salts thereof.
7. A method according to claim 5 which uses an adenine derivative represented by the formula:
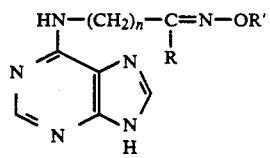
(wherein n represents 1 or 2, and R and R' represent hydrogen, or a methyl, ethyl, allyl, or propargyl group) or agriculturally acceptable acid addition salts thereof for enhancing rooting of the plant to be treated.
* * * * *